(12) United States Patent  
Kagermeier et al.

(10) Patent No.: US 7,956,726 B2  
(45) Date of Patent: Jun. 7, 2011

(54) RADIO OPERATING SYSTEM AND METHOD FOR OPERATING A RADIO SYSTEM

(75) Inventors: Robert Kagermeier, Nürnberg (DE); Donal Medlar, Weisendorf (DE); Dietmar Sierk, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 858 days.

(21) Appl. No.: 10/568,197

(22) PCT Filed: Jul. 16, 2004

(86) PCT No.: PCT/EP2004/007954  
§ 371 (c)(1),  
(2), (4) Date: Feb. 9, 2006

(87) PCT Pub. No.: WO2005/018242  
PCT Pub. Date: Feb. 24, 2005

(65) Prior Publication Data  
US 2006/0244627 A1    Nov. 2, 2006

(30) Foreign Application Priority Data  
Aug. 11, 2003   (DE) ................................ 103 36 731

(51) Int. Cl.  
*G05B 11/01* (2006.01)  
*G05B 19/00* (2006.01)  
*B60R 25/00* (2006.01)

(52) U.S. Cl. ................. 340/13.24; 340/12.5; 340/12.51; 340/5.64; 340/5.72

(58) Field of Classification Search .................. 340/825, 340/69, 825.72, 539.12, 539.15, 5.64, 5.72, 340/572.1; 348/734, 211.1, 211.2; 709/224; 725/39, 46; 341/176, 173  
See application file for complete search history.

(56) References Cited

U.S. PATENT DOCUMENTS 5,289,163 A * 2/1994 Perez et al. .............. 340/539.32  
(Continued)

FOREIGN PATENT DOCUMENTS

DE        43 00 600 A1    7/1994  
(Continued)

OTHER PUBLICATIONS

International Preliminary Report on Patentability (IPER) with English Translation dated Oct. 24, 2005.

*Primary Examiner* — Brian A Zimmerman  
*Assistant Examiner* — Nam V Nguyen  
(74) *Attorney, Agent, or Firm* — Lempia Summerfield Katz LLC

(57) ABSTRACT

A radio operating system, in particular for a medical device, comprises: a radio base station, provided for control of a device, an operating unit, for establishment of a radio connection with the radio base station, whereby the operating unit comprises a controller with a first threshold value (S1) relating to a reception parameter (K), depending on which a switching between various operational modes (B0, B1) for the operating unit is provided. On dropping below the threshold value (S1), a safety-oriented operating mode (B0) and, on exceeding the threshold value (S1), a standard operating mode for the operating element (3), are provided. A first non-safety-critical command set (BS1) may be activated by the operating unit and equally used in the various operating modes (B0, B1), a second safety-critical command set (BS2), activated by means of the operating unit, may be used in the safety-oriented operating mode (B0) in a limited manner in comparison to the standard operating mode (B1).

24 Claims, 2 Drawing Sheets

U.S. PATENT DOCUMENTS

| | | | |
|---|---|---|---|
| 5,379,033 A * | 1/1995 | Fujii et al. | 340/5.64 |
| 5,600,323 A * | 2/1997 | Boschini | 341/173 |
| 5,722,046 A * | 2/1998 | Serfaty et al. | 340/7.35 |
| 5,956,655 A * | 9/1999 | Suzuki et al. | 455/566 |
| 5,957,776 A * | 9/1999 | Hoehne | 463/25 |
| 5,999,229 A * | 12/1999 | Samarughi et al. | 348/634 |
| 6,275,141 B1 * | 8/2001 | Walter | 340/5.64 |
| 6,512,462 B1 * | 1/2003 | Robineau | 340/825.72 |
| 6,624,758 B1 * | 9/2003 | Omata et al. | 340/426.36 |
| 6,651,900 B1 * | 11/2003 | Yoshida | 239/72 |
| 6,753,790 B2 * | 6/2004 | Davies et al. | 340/825.69 |
| 6,903,655 B2 * | 6/2005 | Stefanik | 340/571 |
| 6,947,101 B2 * | 9/2005 | Arling | 348/734 |
| 7,054,594 B2 * | 5/2006 | Bloch et al. | 455/41.2 |
| 7,120,922 B2 * | 10/2006 | Rodriguez et al. | 725/39 |
| 7,336,174 B1 * | 2/2008 | Maloney | 340/572.1 |
| 2001/0038328 A1 | 11/2001 | King et al. | |
| 2003/0139177 A1 | 7/2003 | Doering et al. | |

FOREIGN PATENT DOCUMENTS

| | | |
|---|---|---|
| DE | 101 16 870 A1 | 10/2001 |
| EP | 0 514 244 A1 | 11/1992 |
| EP | 1 312 332 A1 | 5/2003 |
| GB | 2 297 667 | 8/1996 |

* cited by examiner

RADIO OPERATING SYSTEM AND METHOD FOR OPERATING A RADIO SYSTEM

BACKGROUND

This application relates to a radio operating system, particularly for use with a medical device, and to a method for operating the radio system.

For operating a device, especially a medical device, such as an X-ray system, an operating control that is not stationary is often provided. A cable-connected operating control is known for instance from European Patent Disclosure EP 0 834 891 A2. From it, the possibility is also known of linking an operating control to a central station in cordless fashion, for instance via an infrared connection. A cordless connection can in principle also be made by means of radio communication. In contrast to an infrared connection, no visual connection would be necessary between the operating control and the central station, or to the device to be triggered. However, that has a disadvantage that a person operating the equipment who, while carrying the operating control, is moving away from the device to be triggered could change the device settings by unintentionally tripping the operating control. Particularly in the case of medical devices, such an event can be extremely safety-critical. For safety-critical functions of medical devices, radio operations are therefore typically not used.

BRIEF SUMMARY

A radio system includes radio base station unit, which may be stationary and an operating unit that may not be stationary; these may be termed the units of the radio system. An expansion by an arbitrary number of additional stationary or portable units is also possible. Without restricting the general applicability, the discussion herein will refer to a single radio base station unit and a single operating unit, between which radio communication is to be established.

The radio communication between the units of the radio system can be made in various operating modes. One of the units, which may be the operating unit, has a control portion with a first threshold value relating to a reception parameter. The reception parameter, for instance a reception quality parameter, relates to the reception field intensity, or in the case of digital radio communication, may relate to the bit error rate of the data received. For classifying the reception quality, both of the reception field intensity and the bit error rate may be used. A measurement or estimate of the distance between the units of the radio system, which may also be used as the reception parameter, may be provided directly by means of a transit time measurement, and/or indirectly by the evaluation of the reception quality. For simplicity, the terms "reception parameter" and "reception quality parameter" are also used for cases in which the reception properties, in particular the reception quality, are characterized by a plurality of parameters.

Depending on whether the reception parameter, such as the reception quality parameter, is greater than or less than the threshold value, the reception quality parameter, a standard operating mode or a safety-oriented operating mode of the radio system is activated. Information transmission in the radio system is possible by means of two different command sets: a first, non-safety-critical command set and a second, safety-critical command set. As long as the operation of the radio system is taking place in the standard operating mode, both command sets are usable without restriction. Conversely, if a switchover is made to the safety-oriented operating mode, for example, when the reception quality becomes worse, or the distance between the units increases beyond the limit set by the threshold value, then only the first, non-safety-critical command set is usable without restrictions. Restrictions are automatically made in the safety-oriented operating mode with respect to use of the second command set.

In an aspect, the second command set is blocked entirely in the safety-oriented operating mode. However, the use of the second command set may be possible in the safety-oriented operating mode, as long as a confirmation input device, such as a confirmation key, is actuated. In a first alternative, the use of the second command set is enabled only during the period of actuation of the confirmation input device. In a second alternative, by the actuation of the confirmation input device in the safety-oriented operating mode, a time slot is initiated within which all the command sets, and hence the full functional scope of the standard operating mode, are enabled. In this circumstance, the confirmation input device has the function of a trigger key. In another aspect, the time slot that has been initiated is reinitiated after the termination of the operating function tripped by one of the command sets and is thus still open, in a further time interval, for subsequent operation requirements with an arbitrary command set. This situation is advantageous when an operating unit is embodied as a cordless pedal switch.

Instead of separating the functions of the operating unit into two command sets from the standpoint of safety, a more finely graduated classification may be expedient, depending on the type of the device to be triggered. For instance, for functions that for safety reasons should be enabled in every case, especially emergency shutoff functions, to the extent they can be tripped by the operating unit, lower thresholds are set with regard to the required reception quality than for other operating functions required for the intended operation of the device.

A visual display of the active operating mode status, and particularly the safety-oriented operating mode status, particularly at the operating element, may be provided. By the automatic activation of the visual display, for instance in the form of a blinking lighted display, the user is alerted, upon switchover from the standard operating mode to the safety-oriented operating mode, and that the reception quality measured as by the unit at its site is decreasing and/or the distance between the units of the radio system are becoming greater. An acoustic warning report may not be output until the user intentionally or unintentionally actuates an input device, especially a key, of the operating unit, in which a function associated with the second, safety-critical command set, is selected.

By means of the visual display, but without an acoustic report in the case of a reception quality below the threshold value, the user carrying the operating element is alerted, in a way that does not disturb other persons, that he/she is located at an extreme end of the communications range. This also accommodates the situations where the range of the radio communication can be diminished by the various damping factors, such as many persons present in one room where the units of the radio system are also located. In such a case, if the reception parameter drops below the threshold value, then the visual display should be understood as an indication to look for a more suitable site for system operation.

When the transit time of a signal forwarded between the units, instead of the reception quality at the site of one of the units of the radio system, is at least primarily determinative for the reception parameter, it is possible, to limit the region in which radio communication between the units is enabled without restriction. It is thus reliably possible to preclude the tripping of safety-critical functions of the device in a radio-based operating environment, which is intended for operating a stationary device set up in one room, by a unit in a neighboring room.

In an aspect, a second threshold value corresponding to a reception parameter may be provided; if the reception parameter is less than the second threshold, the radio communication between the units is disabled or terminated. Regardless of whether the termination of the radio communication is based on the second threshold value or solely based on given physical conditions, especially an excessive distance between the units, an acoustic report may be output that informs the user about the termination of the radio communication. The threshold may not be fixed. This makes it possible to prevent a user from unintentionally carrying the operating unit out of reception range, for instance in his/her pocket.

In a situation where there is complete or partial blocking of part of the functional scope of a radio-operated device, such as where the radio reception quality drops below the threshold value or a distance between units is too great, as ascertained by transit time measurement, the use of the radio operating element remains limited in the desired way to the near vicinity of the device, in particular the medical device, that is to be triggered.

BRIEF DESCRIPTION OF THE DRAWINGS

An example is described in further detail below with reference to the drawings.

DETAILED DESCRIPTION OF THE DRAWINGS AND THE PRESENTLY PREFERRED EMBODIMENTS

Reference will now be made in detail to embodiments, but it will be understood that it is not intended to limit the invention to such embodiments. In the following description, numerous specific details are set forth in order to provide a thorough understanding of the present invention which, however, may be practiced without some or all of these specific details. In other instances, well known process operations have not been described in detail in order not to unnecessarily obscure the description.

Figure 1:
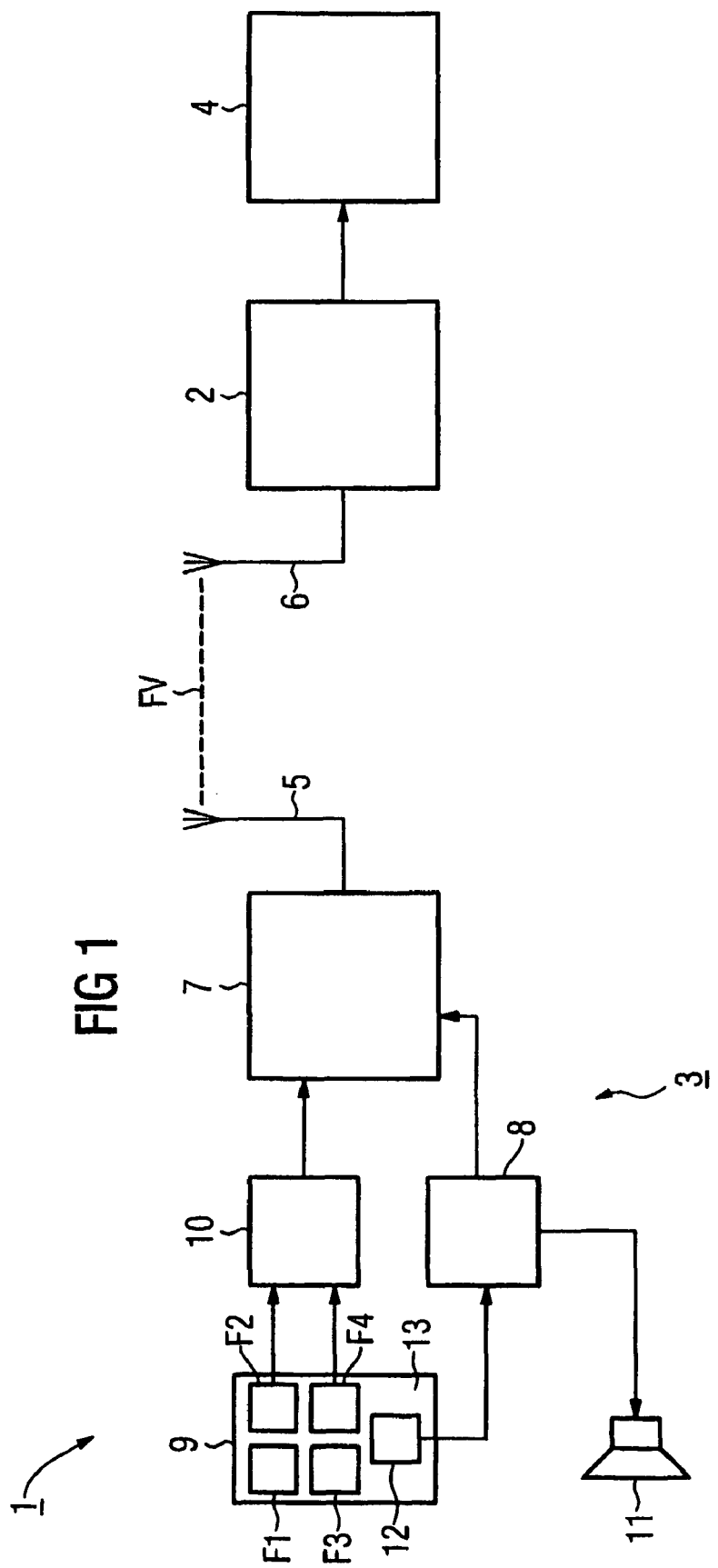
FIG. 1 shows a radio operating system for a medical device.
Figure 2:
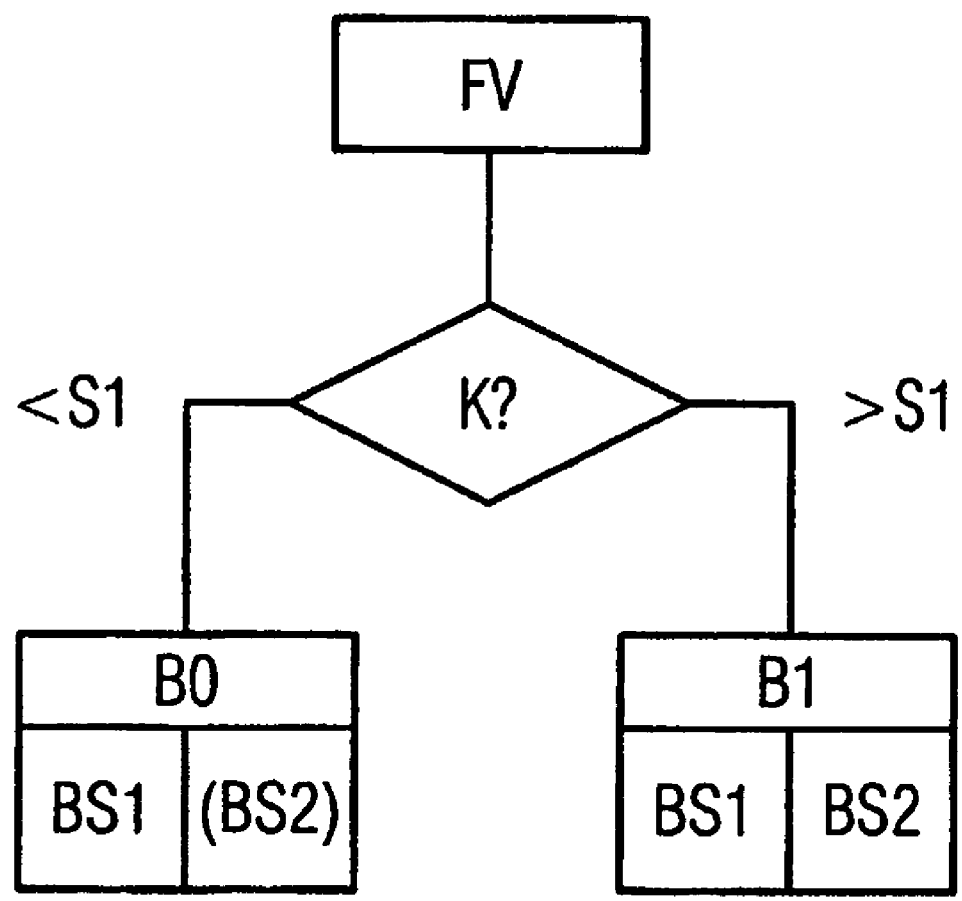
FIG. 2, in a flow chart, shows various operating states of the radio operating system of FIG. 1.

As shown in FIG. 1, a radio operating system 1 includes a stationary radio base station unit 2 and a portable operating unit 3. A medical device 4 to be triggered, such as an X-ray system or lithotripsy system, is connected to the radio base station unit 2. The functional scope of the device 4 includes safety-relevant functions, such as switching drives or radiation sources, and functions that are not relevant to safety, such as display functions. Both safety-critical and non-safety-critical functions of the device 4 can be controlled by means of the operating unit 3. Radio communication between the operating unit 3 and the radio base station unit 2 is established by means of antennas 5, 6; the maximum communications range is approximately 5 to 8 meters. The user actuating the operating unit 3 may work under the safety rule of maintaining a visual connection with the device 4 to be triggered and thus, in general, also with the radio base station unit 2, which may be installed on or in the device 4. In an aspect, should the radio base station 2 be covered by a cloth hanging down from an examination table, there may be practically no impairment to the radio communication, which is shown in dashed lines and marked FV. In this aspect, the radio communication between the radio base station unit 2 and the operating unit 3 offers significant advantages, for instance, over an infrared connection. On the other hand, however, the possibility that the user by unintentionally actuating the operating unit 3 without visual contact with the device 4, for instance in an antechamber to the examination chamber or to the operating room where the device 4 is set up, and undesirably activate functions of the device 4 cannot be precluded. This danger is effectively counteracted by operating the operating unit 3 in operating modes B0, B1, described in further detail below, and also with reference to the flow chart of FIG. 2.

The operating unit 3 has a radio module 7, which furnishes information about the field intensity, measured by means of the antenna 5, and about the bit error rate of the received data to a control portion ("controller") 8. In addition or as an alternative, the distance between the antennas 5, 6 of the units 2, 3 is ascertained by transit-time measurement in the radio operating system 1.

The controller 8 is also connected to a keypad 9, a keypad controller 10, and a speaker 11 as an acoustic output device. In an example, keypad 9 includes four function keys F1, F2, F3, and F4. The designations F1 through F4 represent the functions of the device 4 that can be triggered by the operating unit 3. In this example, the functions F1, F2 are assigned to a first, non-safety-critical command set BS1, and the functions F3, F4 are assigned to a second, safety-critical command set BS2. As long as the user carrying the operating unit 3 is within the communications range of the system, and no significant shields are in the way, all the functions F1 through F4 are enabled without restriction: the operating unit 3 is in the standard operating mode B1.

As the distance between the operating element 3 and the radio base station 2 increases, and/or if there are shields between the units 2, 3, for instance in the form of a wall in a building, the reception quality of the data stream originating at the radio base station unit 2, which quality is detectable by means of the antenna 5 of the operating unit 3, becomes worse. The reception quality at the operating unit 3 is converted, by measuring the field intensity and/or ascertaining the bit error rate, into at least one reception quality parameter ("reception parameter" or "reception quality parameter") K, which serves the controller 8 as an input variable. Alternatively, the reception parameter K is a measure of the distance between the units 2, 3 of the radio system, and a decreasing reception parameter K corresponds to an increasing spacing between the units 2, 3. The controller 8 compares the parameter K, generated by the radio module 7, with a first threshold value S1.

The allocation of functions into the radio module 7 on the one hand and the controller 8 on the other should be understood as merely symbolic. A plurality or all of the components, that is, the radio module 7, controller 8 and keypad controller 10, may be realized as one integral component, and both open- and closed-loop control functions can also be attained by software. It is equally possible as an alternative, for functions shown symbolically inside the operating unit 3 also to be integrated with the radio base station unit 2 and/or the device 4.

If the reception parameter K is less than the first threshold value S1, a further, safety-oriented operating mode B0 is activated. The functions F1, F2 associated with the first, non-safety-critical command set BS1 are enabled without change. However, the functions F3, F4 associated with the second, safety-critical command set BS2 are not usable merely by actuating the corresponding keys of the operating unit 3.

Instead, to enable the safety-critical functions F3, F4, the actuation of an enabled key 12, as a confirmation input device, is required.

In a first alternative, the use of the functions F3, F4 of the safety-critical command set BS2 is enabled only so long as the enable key 12 continues to be depressed. In a second alternative, the full functional scope of the standard operating mode B1 that includes both command sets BS1, BS2 is enabled, for instance for a period of 10 seconds, by a brief actuation of the enable key 12. The user is informed of the necessity of actuating the enable key 12 by an acoustic warning signal output by the speaker 11, as soon as the user selects one of the functions F3, F4 in the safety-oriented operating mode B0 without having first enabled the functions. In this way, the user is precluded from unintentionally tripping a safety-critical function of the device 4. The restricted use of functions, only after actuation of the enable key 12 for the safety-critical command set BS2 in the safety-oriented operating mode B0, is symbolized in FIG. 2 by the term BS2.

When the user, carrying the operating unit 3, moves out of the near vicinity of the radio base station 2 within which the standard operating mode B0 is possible, an acoustic warning is not automatically given. The safety-oriented operating mode B0 activated and the activation of the safety-oriented operating mode B0 is displayed by a light-emitting diode 13 as a visual display device in an undisturbing way. If only the functions F1, F2 associated with the non-safety-critical command set BS1 are selected, no acoustic warning is made. But, the user is informed of the fact that he/she is located in a region of reduced reception field intensity and/or an increased bit error rate by the visual display. In this way, great user friendliness of the radio operating system 1 is provided.

If the operating unit 3 is moved farther from the radio base station unit 2, or the reception quality of the location of the antenna 5 is further reduced in some other way, then the parameter K drops below a threshold value S2 specified in the controller 8. In that case, all the functions F1 through F4 are blocked. Information to the user is accordingly provided by an acoustic warning, output via the speaker 11. The acoustic signal may be, for instance, a defined sequence of tones, or speech output. If the operating unit 3, in addition to the keypad 9, or combined with the operating unit 3, may also have an optical output device, for instance in the form of a touch sensitive display screen, then the output of an visual report, for instance in the form of a clear text display, may be provided in addition or alternatively to the acoustic warning.

Although the present invention has been explained by way of the examples described above, it should be understood to the ordinary skilled person in the art that the invention is not limited to the examples, but rather that various changes or modifications thereof are possible without departing from the spirit of the invention. Accordingly, the scope of the invention shall be determined only by the appended claims and their equivalents.

The invention claimed is:

1. A radio operating system, comprising:
a radio base station unit configured to control a device; and
an operating unit in radio frequency (RF) communication with the radio base station unit,
wherein a selection is provided between a plurality of operating modes of the operating unit, the selection corresponding to a value of a reception parameter with respect to a first threshold value and a second threshold value;
when the reception parameter value is less than the first threshold value, a first operating mode is selected and when the reception parameter is greater than the first threshold value, a second operating mode is selected; a first, non-safety-critical command set, is usable in each of the first operating mode and the second operating mode; a second, safety-critical command set, is usable in the second operating mode; and when the reception parameter is less than the second threshold value, the first operating mode and the second operating mode are blocked.

2. The radio operating system as in claim 1, wherein actuation of a confirmation input device, enables the second, safety-critical command set.

3. The radio operating system as in claim 1, wherein the operating unit has a display device provided for displaying the operating mode.

4. The radio operating system as in claim 1, wherein the operating unit has an acoustic output device.

5. The radio operating system as in claim 1, wherein when the reception parameter is less than the second threshold value, the RF connection between the operating unit and the radio base station unit is disabled.

6. The radio operating system as in claim 2, wherein the operating unit has a display device provided for displaying the operating mode.

7. The radio operating system as in claim 2, wherein the operating unit has an acoustic output device.

8. The radio operating system as in claim 7, wherein when the reception parameter is less than the second threshold value, the radio connection between the operating unit and the radio base station unit is disabled.

9. A method for operating a radio system having at least two units, the method comprising:
measuring a transmission quality of a radio frequency (RF) communication between the at least two units to determine a reception parameter;
comparing a value of the reception parameter with a first threshold value and a second threshold value;
selecting one operating mode of a plurality of operating modes as a function of the value of the reception parameter with respect to the first threshold value and the second threshold value, wherein a first operating mode is selected when the value of the reception parameter is less than the first threshold value, a second operating mode is selected when the value of the reception parameter is greater than the first threshold value, and no operating mode of the plurality of operating modes is selected when the reception parameter is less than the second threshold value;
providing a first, non-safety-critical command set, and a second, safety-critical command set;
enabling the use of the second, safety-critical command set and the first, non-safety critical command set in the second operating mode; and
enabling the first, non-safety-critical command set in the first mode, and restricting the use of the second, safety-critical command set.

10. The method as in claim 9, wherein the second, safety-critical command set is enabled in the first operating mode by actuation of a confirmation input device.

11. The method as in claim 10, wherein the use of the second, safety-critical command set is enabled in the first operating mode during the period of actuation of the confirmation input device.

12. The method as in claim 10, wherein the actuation of the confirmation input device in the first operating mode opens a time slot, within which the second, safety-critical command set is enabled.

13. The method as in claim 10, wherein upon switchover from the second operating mode to the first operating mode, an optical report is output.

14. The method as in claim 10, wherein when a function associated with the second, safety-critical command set is chosen in the first operating mode, an acoustic warning is output.

15. The method as in claim 10, wherein if the RF communication between the at least two units is disabled because of the transmission quality, an acoustic signal is output.

16. The method as in claim 10, wherein the reception parameter contains information representing a reception quality of the RF communication between the at least two units.

17. The method as in claim 9, wherein upon switchover from the second operating mode to the first operating mode, an optical report is output.

18. The method as in claim 9, wherein when a function associated with the second, safety-critical command set is chosen in the first operating mode, an acoustic signal is output.

19. The method as in claim 9, wherein if the RF communication between the at least two units is disabled because of the transmission quality, an acoustic signal is output.

20. The method as in claim 9, wherein the reception parameter contains information representing the reception quality of the RF communication between the at least two units.

21. The method as in claim 20, wherein the reception parameter contains information representing a reception RF field intensity at a location of one of the at least two units.

22. The method as in claim 20, wherein the reception parameter includes information representing a bit error rate of the RF communication between the at least two units.

23. The method as in claim 9, wherein the reception parameter includes information representing a distance between the at least two units.

24. The method as in claim 23, wherein the reception parameter is ascertained by transit time measurement.

* * * * *